United States Patent [19]

Bradstock et al.

[11] Patent Number: 5,158,885
[45] Date of Patent: Oct. 27, 1992

[54] MOUSE MONOCLONAL ANTIBODIES RAISED TO THE T-CELL LINE HSB-2 AND T-CELL CHRONIC LYMPHOCYTIC LEUKEMIA (T-CLL) CELLS REACT WITH NORMAL HUMAN T AND B LYMPHOCYTES AND MONOCYTES

[75] Inventors: Kenneth F. Bradstock, Drummoyne; Michael K. Atkinson, Palm Beach; Anthony J. Henniker, Wahroonga, all of Australia

[73] Assignee: Biomedical Systems Ltd, Australia

[21] Appl. No.: 477,956

[22] PCT Filed: Oct. 14, 1988

[86] PCT No.: PCT/AU88/00400

§ 371 Date: May 23, 1990

§ 102(e) Date: May 23, 1990

[87] PCT Pub. No.: WO89/03397

PCT Pub. Date: Apr. 20, 1989

[30] Foreign Application Priority Data

Oct. 16, 1987 [AU] Australia ................ PI4910

[51] Int. Cl.$^5$ .................... C12N 5/20; C07K 15/28
[52] U.S. Cl. .................... 435/240.27; 530/388.7; 530/388.73; 530/388.75
[58] Field of Search ............ 435/240.27; 530/387, 530/388.7, 388.73, 388.75

[56] References Cited

PUBLICATIONS

Becker et al., "Monoclonal Antibodies to Human Macrophage and Leucocyte Common Antigens," *Pathology*, 13, 669–680 (1981).

Vaughan et al., "Hu Ly-m3-A Human Leukocyte Antigen," *Transplantation*, 36, 446–450 (1983).

Hale et al., "Removal of T Cells from Bone Marrow for Transplantation: A Monoclonal Antilymphocyte Antibody That Fixes Human Complement," *Blood*, 62, 873–882 (1983).

*Primary Examiner*—John J. Doll
*Assistant Examiner*—George C. Elliott
*Attorney, Agent, or Firm*—Christie, Parker & Hale

[57] ABSTRACT

The prevent invention relates to two monoclonal antibodies which are broadly reactive with all normal human peripheral blood T and B lymphocytes and monocytes and to hybridoma cell lines which produce these monoclonal antibodies. These monoclonal antibodies are designated WM-66 and WM-63 and the respective hybridoma cell lines are designated F56-2D7 (ECAC 88101104) and F56-4D6 (ECACC 88101103). Both of these monoclonal antibodies react with a previously unrecognized human leucocyte differentiation antigen. The relative molecular mass of the antigen recognized by WM-66 is approximately 65 kilodaltons.

4 Claims, No Drawings

MOUSE MONOCLONAL ANTIBODIES RAISED TO THE T-CELL LINE HSB-2 AND T-CELL CHRONIC LYMPHOCYTIC LEUKEMIA (T-CLL) CELLS REACT WITH NORMAL HUMAN T AND B LYMPHOCYTES AND MONOCYTES

FIELD OF THE INVENTION

The present invention relates to two new hybridoma cell lines and to monoclonal antibodies produced by these hybridoma cell lines. Both these monoclonal antibodies exhibit broad range reactivity with human leucocytes, and have potential for use as immunosuppressive agents.

BACKGROUND OF THE INVENTION

Since it was shown by Kohler and Milstein (Nature Vol. 256, 495–497, 1975) that it was possible to fuse mouse myeloma cells with spleen cells from immunized mice and thereby produce a continuous cell line which produces a homogeneous (monoclonal) antibody, extensive attention has been focused on the production of these hybrid cell lines (hybridomas) and the monoclonal antibodies (Mabs) produced.

The development of hybridoma technology has led to a drammatically improved understanding of the antigenic molecules on the surface of human leucocytes. Much of this information has recently been systematised in the International Workshop on Human Leucocyte Differentiation Antigens, and the majority of many thousands of Mabs reported can now be recognised as belonging to one of the 45 accepted Clusters of Differentiation (CD). The majority of these clusters define antigens which are restricted to specific leucocyte differentiation lineages or to maturation stages. One group of Mabs, however, belonging to CD 45, define a 200 kilodalton protein, now known as Leucocyte Common Antigen (LCA) or T-200, which has the unusual property of being expressed on virtually on human leucocytes.

There are only a few other molecules with a similar distribution. Class I histocompatibility antigens are found on all leucocytes (with the exception of immature thymocytes), but are also expressed on a wide variety of non-haemopoietic tissue. Two other antigens, identified by Mabs CAMPATH-1 (Blood, 1983; 62:873) and Hu-LyM3 (Transplantation; 1983 36:446) also have pan-haemopoietic distribution, although their expression on non-haemopoietic cells is less certain.

SUMMARY OF THE INVENTION

In a first aspect the present invention consists in a mouse monoclonal antibody of Class IgM produced by a hybridoma formed by fusion of cells from a mouse myeloma line and spleen cells from a mouse previously immunized with the T cell line HSB-2 and T-CLL cells, the monoclonal antibody being characterised in that it reacts with leucocyte differentiation antigen of a relative molecular weight of approximately 65 kilodaltons which is expressed on over 90% of normal human peripheral blood mononuclear cells but not on normal granulocytes, platelets or erythrocytes, and that it is essentially unreactive with human leukaemic cells either from fresh cases of acute leukaemia or the commonly available leukaemic cell lines of B, T and myeloid derivation.

It is preferred that the monoclonal antibody is further characterised in that it:

(a) Reacts with approximately 95% of normal human thymocytes;

(b) Reacts with greater than 97.5% of tonsil lymphocytes;

(c) Reacts with approximately 95% of activated human lymphocytes;

(d) Fixes both human and rabbit complement; and

In a second aspect the present invention consists in an IgM monoclonal-antibody-producing hybridoma cell line formed by fusion of cells from a mouse myeloma line and spleen cells from a mouse previously immunized with the T cell line HSB-2 and T-CLL cells, the monoclonal antibody produced being characterised in that it reacts with a leucocyte differentiation antigen of a relative molecular weight of approximately 65 kilodaltons which is expressed on over 90% of normal human peripheral blood mononuclear cells but not on normal granulocytes, platelets or erythrocytes and that it is essentially unreactive with human leukaemic cells either from fresh cases of acute leukaemia or the commonly available leukaemic cell lines of B,T and myeloid derivation.

It is preferred that the monoclonal antibody produced is further characterized in that it:

(a) Reacts with approximately 95% of normal human thymocytes;

(b) Reacts with greater than 97.5% of tonsil lymphocytes;

(c) Reacts with approximately 95% of activated human lymphocytes;

(d) Fixes both human and rabbit complement.

The monoclonal antibody of the first aspect of the present invention has been designated WM-66, and the hybridoma cell line of the second aspect of the present invention has been designated F56-2D7. This hybridoma cell line was deposited with the European Collection of Animal Cell Cultures (ECACC) on 11 October 1988 and was accorded accession number 88101104. The disclosure of this deposit is herein incorporated by way of cross-reference. The monoclonal antibody of the first aspect of the present invention will hereafter be referred to as WM-66 and the hybridoma cell line of the second aspect of the present invention will hereafter be referred to as F56-2D7.

In a third aspect the present invention consists in a mouse monoclonal antibody of Class IgM produced by a hybridoma cell line formed by a fusion of cells from a mouse myeloma line and spleen cells from a mouse previously immunized with the T cell line HSB-2 and T-CLL cells, the monoclonal antibody being characterised in that it:

(a) Reacts with essentially all normal human peripheral blood T and B lymphocytes and monocytes, but not wit normal human granulocytes, erythrocytes or platelets;

(b) Reacts with approximately 40% to approximately 55% of normal human thymocytes;

(c) Reacts with approximately 90% of normal tonsil lymphocytes;

(d) Reacts with leukaemic cells from patients with B cell chronic lymphatic leukaemia as well as a proportion of cases of acute myeloid leukaemia;

(e) Reacts with the human T cell leukaemia lines T-ALL, MOLT-4, and HSB-2;

(f) Reacts with human B cell lines Raji, Daudi and Bristol-8;

(g) Reacts with the human myeloid cell lines HL-60, Rc2a, U937;

(h) Reacts with 90% of mitogen activated human lymphocytes; and (i) Fixes both human and rabbit complement.

In a fourth aspect the present invention consists in an IgM monoclonal-antibody-producing hybridoma cell line formed by a fusion of cells from a mouse myeloma line and spleen cells from a mouse previously immunized with the T cell line HSB-2 and T-CLL cells, the monoclonal antibody produced being characterised in that it:

(a) Reacts with essentially all normal human peripheral blood T and B lymphocytes and monocytes, but not with normal human granulocytes, erythrocytes or platelets;

(b) Reacts with approximately 40% to approximately 55% of normal human thymocytes;

(c) Reacts with approximately 90% of normal tonsil lymphocytes;

(d) Reacts with leukaemic cells from patients with B cell chronic lymphatic leukaemia as well as a proportion of cases of acute myeloid leukaemia;

(e) Reacts with the human T cell leukaemia lines T-ALL, MOLT-4, and HSB-2;

(f) Reacts with human B cell lines Raji, Daudi and Bristol 8;

(g) Reacts with the human myeloid cell lines HL-60, Rc2a, U937;

(h) Reacts with 90% of mitogen activated human lymphocytes; and (i) Fixes both human and rabbit complement.

The monoclonal antibody of the third aspect of the present invention has been designated WM-63 and the hybridoma cell line of the fourth aspect of the present invention has been designated F56.4D6. This hybridoma cell line was deposited with the European Collection of Animal Cell Cultures (ECACC) on Oct. 11, 1988 and was accorded accession number 88101103. The disclosure of this deposit is hereby incorporated by way of cross reference.

Hereafter the monoclonal antibody of the third aspect of the present invention will be referred to as WM-63 and the hybridoma cell line of the fourth aspect of the present invention will be referred to as F56.4D6.

DETAILED DESCRIPTION OF THE INVENTION

Both hybridoma cell lines F56.2D7 and F56 4D6 were produced using the same technique which is described in detail below. The monoclonal antibodies WM-66 and WM-63 produced by these hybridoma cell lines were tested using the techniques described below.

Immunization and Hybridoma Production

An 8 week old female BALB/c mouse was immunized intraperitoneally with $10^7$ cells of the T cell leukaemia line HSB-2. This was followed 5 days later by an intraperitoneal injection of $5 \times 10^6$ peripheral blood cells from a patient with a T cell form of chronic lymphatic leukaemia (T-CLL). After a final immunization of $8 \times 10^6$ T-CLL cells on day 20, the spleen was removed on day 23, and splenic lymphocytes fused with P3-NS1-Ag3 mouse myeloma cells using 40% polyethylene glycol, according to known methods. Cells were distributed in microtitre plates (Linbro) in Dulbeccos minimal essential medium containing hypoxanthine-aminopterin-thmidine (Flow Labs), 10% foetal calf serum (Flow Labs), L-glutamine and antibiotics. Hybridomas selected in this medium were tested for monoclonal antibody secretion by immunofluorescence reactivity of supernatant medium on human peripheral blood lymphocytes. Two hybridomas, F56-2D7 and F56-4D6 were subsequently cloned three times by limiting dilution technique, and monoclonal antibodies prepared from each hybridoma by intraperitoneal injection of cloned hybridoma cells into Pristane-primed mice, and collection of ascites.

Preparation of Human Cells for Antibody Characterization

Mononuclear cells were isolated from peripheral blood samples of normal volunteers after Ficoll-Hypaque (Pharmacia) centrifugation. Normal granulocytes were isolated from similar samples using Monopoly medium (Flow Labs). Normal tonsil and thymic lymphocytes were obtained from fresh surgical samples, which were dissected and teased into tissue culture medium to obtain cell suspensions. Leukaemic cells were taken from cryopreserved stocks of bone marrow or peripheral blood diagnostic samples, purified on Ficoll-Hypaque before freezing. Leukaemic cell lines were maintained in RPMI-1640 medium supplemented with 10% foetal calf serum at concentrations required to keep cells in log growth phase.

Immunofluorescence Staining and Flow Cytometry

Leucocytes were prepared for immunofluorescence analysis using known methods. Briefly, $1.2 \times 10^6$ cells were reacted with saturating concentrations of monoclonal antibodies at 20° C. for 10 minutes, washed twice in phosphate buffered saline with 0.01% sodium azide (PBSA), and, where appropriate, then incubated with sheep antiserum to mouse immunoglobulin conjugated with fluroscein isothiocyanate (SAM-FITC; Silenus). In some experiments, Mabs directly conjugated with FITC or with phycoerythrin (PE) were used. After two further washes in PBSA, cells were analyzed in a FACS 440 flow cytometer (Becton Dickinson, Calif.), using the 488nM line of an argon laser. Controls consists of isotype-specific irrelevant Mabs, with identical SAM-FITC staining of cells.

Complement-Mediated Cytotoxicity

The lytic ability of Mabs was tested using freshly isolated peripheral blood mononuclear cells as targets. $1 \times 10^6$ cells in RPMI-1640 medium were incubated with Mab for 15 minutes at room temperature, then mixed without washing with an equal volume of either rabbit serum (Pelfreez) or pooled normal human serum. After incubation at 37° C. for 45 minutes, cell viability was assessed by Trypan blue exclusion.

Cell Proliferation Assays

The ability of peripheral blood lymphocytes to proliferate after lytic treatment with Mab and complement was determined by stimulation with the lectin phytohaemagglutinin (PHA) (Pharmacia). $1 \times 10^6$ lymphocytes were treated with Mab and complement as above, then immediately plated in triplicate in microtitre wells in RPMI-1640 medium containing 20% heat inactivated human AB serum, and 10 ug/ml PHA. After 3 days incubation at 37° C. in 5% $CO_2$ in air, wells were pulsed with $^3$-H-thymidine (Amersham, 1 micro Curie per well) for 18 hours. Cells were then washed, and assayed for tritiated thymidine incorporation in a beta scintillation counter. Controls consisted of positively reactive Mab WM-60 (anti-HLA Class 1) or negative irrelevant Mab.

Bone Marrow Progenitor Assays

Fresh bone marrow was obtained with the consent of normal healthy donors undergoing bone marrow harvest for allogeneic transplantation. Marrow was centrifuged on Ficoll-Hypaque (as described above) to obtain mononuclear cells. $1 \times 10^6$ viable cells were then incubated with a saturating concentration of sterile WM-66, sterile WM-63 or with WM-60 (anti-MHC Class 1) or WMD-1 (negative control) for 30 minutes at 4° C. with intermittent agitation, then mixed with an equal volume of rabbit serum (Pelfreez) and incubated at 37° C. for 60 minutes. $1 \times 10^6$ viable cells were then plated out in quadruplicate in 0.3% agar containing 25% foetal calf serum (Flow) in 35mm Petri dishes, with an 0.5% agar underlayer containing $1 \times 10^6$ irradiated normal peripheral blood mononuclear cells as a feeder layer. Plates were incubated in 5% $CO_2$ in air at 37° C., and examined at day 12 under an inverted microscope. Colonies were scored as groups of more than 40 cells.

Immunoprecipitation and Electrophoresis

Immunochemical identification of antigens was performed according to known methods. Cell surface labelling was performed using peripheral blood mononuclear cells and $Na^{125}I$ (New England Nuclear), using the lactoperoxidase method, as previously described. Cells were then lysed in EHS buffer (0.01 Hepes, 0.15M sodium chloride, 5mM EDTA, pH7.4) containing 8ug di-isopropyl-fluorophosphate (Sigma), 100 ug leupeptin (Sigma) and 100 ul 11% Triton X-100 on ice. Cytoskeletal material was removed by centrifugation, and the lystate precleared overnight using Pansorbin (Calbiochem). The lysate was centrifuged and incubated with 10ug purified Mab for 2 hours at 4° C., followed by incubation with 50ug of goat-anti-mouse immunoglobulin of the appropriate subclass (Cappell) for 30 minutes at 4° C. The material was centrifuged and the pellet resuspended in non-reduced electrophoresis buffer. Reduced samples were prepared by addition of 15 ul mercaptoethanol.

One dimensional electrophoresis of samples, either reduced or non-reduced, was carried out on a 5–20% polyacrylamide gel, using molecular weight markers (Biorad) run in conjunction. Gels were stained with 0.1% Coomassie Brilliant Blue, dried and autoradiography performed using Hyperfilm x-ray film (Amersham) at −70° C.

Tissue Section Staining

Fresh biopsy tissues were snap frozen in isopentane and stored in liquid nitrogen. Cryostat sections 6 to 8 microns thick were air-dried on poly-L-Lysine (Sigma) treated slides, and fixed in absolute acetone at −10° C. for 5 minutes, then washed in 3% hydrogen peroxide in 0.05M Tris-HCl-phosphate buffered saline (pH7.6) for 5 minutes to block endogenous peroxidase. Tissue sections were then washed in Tris buffered saline for 15 minutes. Prior to immunohistochemical staining, sections were incubated with diluted normal horse serum (Vectastain ABC Kit, no. PK-4002) for 5 minutes to reduce non-specific binding of the secondary antibody. Mab WM-66, or the isotype specific negative control Mab, WMD-1, in the form of 1:10 dilution of culture supernatant was then added over sections, and incubated for 1 hour in a humidified chamber on a platform rocker. Slides were then washed in Tris-PBS, then incubated with an appropriate dilution of biotinylated horse anti-mouse antibody (Vectastain) for 20 minutes. After further washing in Tris-PBS, sections were incubated for 30 minutes with avidin horseradish peroxidase H complex (Vectastain), washed, then developed for 4 minutes in DAB solution (0.03% 3,3′-daiminobenzidine tetrahydrochloride (Fluka, Switzerland) and 0.2 mM imidazole (Sigma) in PBSA). After further washing in water for 5 minutes, sections were counterstained with Mayer's haematoxylin and blueing solution, before dehydration in absolute alcohol, clearing in xylol and mounting.

RESULTS

Cellular Reactivity of WM-66 MAB

The cloned hybridoma cell line F56-2D7 secreted a monoclonal antibody, which was subsequently shown to be a murine IgM using sub-class specific antisera (Nordic). This Mab was subsequently designated WM-66.

The reactivity of WM-66 with normal and leukaemic haemopoietic cells is given in Table. 1. WM-66 bound to over 90% of normal peripheral blood mononuclear cells, but not to normal granulocytes, platelets, or erthrocytes. Peripheral blood mononuclear cells were analyzed by two-colour flow cytometry using FITC-conjugated WM-66 and PE-labelled Mabs recognizing antigens specific to T,B, and monocytic lineages. These experiments confirmed that WM-66 labelled virtually all monocytes as well as T and B lymphocytes in peripheral blood. The majority of thymic and tonsil lymphocytes were also positively stained with WM-66, as was a sub-population of normal bone marrow leucocytes. The latter included a minority of normal myeloid progenitor cells, as pretreatment of bone marrow with WM-66 and complement produced 40% inhibition of granulocyte-macrophage colony (Table 2). WM-66 was reactive with T lymphoblasts derived from 3 day PHA-stimulated cultures of normal peripheral blood lymphocytes, at equivalent staining intensity to unstimulated cells.

The reactivity of WM-66 with leukaemic cells and cell lines is also detailed in Table 1. Only cases of B-cell chronic lymphatic leukaemia (B-CLL), B-cell lymphoma in leukaemic phase, hairy cell leukaemia, and 1 case of T-CLL (the original immunogen) were WM-66-positive. Virtually all cases of acute lymphoblastic and myeloid leukaemia, as well as all haemopoietic and non-haemopoietic cell lines tested, were negative.

TABLE 1

REACTIVITY OF WM-66 MAB WITH NORMAL AND LEUKAEMIC HAEMOPOIETIC CELLS

| CELL TYPE | PERCENT POSITIVE[a] |
|---|---|
| (A) NORMAL CELLS | |
| Peripheral blood mononuclears | |
| T lymphocytes (CD-3+) | 89.8 +/− 4.1 (n = 5) |
| B lymphocytes (CD-20+) | 95.0 +/− 3.8 (n = 5) |
| Monocytes | 94.8 +/− 2.9 (n = 5) |
| Granulocytes | 1 (n = 5) |
| Platelets | 1 (n = 5) |
| Erythrocytes | 1 (n = 5) |
| Thymocytes | 95 (n = 2) |
| Tonsil lymphocytes | 97.5 (n = 2) |
| Bone marrow mononuclears | 38 (n = 1) |
| (B) LEUKAEMIC CELLS | |
| B-CLL[c] | 5/5[b] |

TABLE 1-continued

REACTIVITY OF WM-66 MAB WITH NORMAL AND LEUKAEMIC HAEMOPOIETIC CELLS

| CELL TYPE | PERCENT POSITIVE[a] |
|---|---|
| Hairy cell leukaemia | 2/2 |
| B lymphoma | 5/7 |
| T-CLL | 1/1 |
| C-ALL | 0/17 |
| T-ALL | 0/10 |
| AML | 2/33 |
| CML | 0/7 |
| (C) LEUKAEMIC CELL LINES | |
| B-cell | 0/3 |
| T-cell | 0/5 |
| Pre-B | 0/3 |
| Myeloid | 0/4 |
| (D) NON-HAEMOPOIETIC CELL LINES | |
| Melanoma | 0/1 |
| Squamous cell carcinoma | 0/2 |
| Fallopian carcinoma | 0/1 |
| Ovarian carcinoma | 0/4 |
| Cervical carcinoma | 0/2 |
| Neuroblastoma | 0/1 |
| Breast carcinoma | 0/1 |

Footnotes
[a]Percentage of cells positive above negative control by indirect immuno-fluorescence. +/− 1 standard deviation.
[b]Number of cases of leukaemia, or number of cell lines, with ≧20% cells positive by indirect immuno-fluorescence, over total number tests.
[c]B-CLL, B form of chronic lymphatic leukaemia; T-CLL, T form of CLL; C-ALL, common or non-T, non-B form of acute lymphoblastic leukaemia; AML, acute myeloid leukaemia; CML, chronic myeloid leukaemia.

TABLE 2

REACTIVITY OF WM-66 WITH NORMAL BONE MARROW MYELOID PROGENITOR CELLS

| TREATMENT OF CELLS | NUMBER OF $CFU_{GM}$[a] | |
|---|---|---|
| | EXPT. 1 (% inhibition) | EXPT. 2 (% inhibition) |
| [b]IRRELEVANT MAB + C[1] | 194 +/− 19.4 | 327.3 +/− 38.1 |
| WM-66 + C[1] | 116 +/− 20.8 (40.3) | 127.0 +/− 4.6 (38.6) |
| WM-60 + C[1] | 0.4 +/− 0.1 (99.8) | 0 (100) |

Footnotes
[a]Mean number of granulocyte-macrophage colonies in quadriplicate plates after 12 days incubation, +/− 1 standard deviation. Percentage inhibition of colony formation indicated in parentheses.
[b]Bone marrow mononuclear cells treated prior to plating with irrelevant Mab (WMD-1), WM-66, or positive MHC Class 1 control (WM-60), and incubated with rabbit complement.

Cytolytic Effect of WM-66 On Lymphocyte Proliferation

On the basis of dye exclusion studies, WM-66 was capable of lysing the majority of peripheral blood mononuclear cells. Using human serum as a source of complement, WM-66 gave a mean 95.0 +/−1.3% (n=5) cytotoxicity, while with rabbit serum there was mean 95.4% +/−3.4% (n=5) killing. When cells treated in this way were subsequently cultured in the presence of 10 ug/ml PHA, there was complete abrogation of the normal proliferative response to this mitogen, indicating that WM-66 was cytotoxic to virtually all mitogen-responsive T lymphocytes (Table 3).

Immunochemical Characterization of the Antigen Recognized By WM-66

Immunoprecipitation and electrophoresis experiments, using $^{125}$I-surface labelling, have indicated that WM-66 recognises a surface protein with relative molecular mass of approximately 65 Kilodaltons, under both reduced and non-reduced conditions.

Non Haemopoietic Tissue Reactivity of WM-66

Frozen sections of normal tissues were evaluated for WM-66 reactivity by immunoperoxidase using avidin-biotin-peroxidase complex. WM-66 reacted strongly with lymphoid cells and macrophages in lymph node. Columnar epithelial cells lining bronchi and salivary gland ducts were also strongly labelled by WM-66. All other tissues tested were negative, including kidney, skeletal muscle, heart, and endothelium.

RESULTS

Cellular Reactivity of WM-63 MAB

The cloned hybridoma cell line F56-4D6 secreted a monoclonal antibody, which was subsequently shown to be a murine IgM using sub-class specific antisera (Nordic). This Mab was subsequently designated as WM-63.

TABLE 3

EFFECT OF MONOCLONAL ANTIBODY TREATMENT OF PHA-INDUCED LYMPHOCYTE PROLIFERATION

| CELL[a] TREATMENT | COUNTS PER MINUTE | | | | | | | | |
|---|---|---|---|---|---|---|---|---|---|
| | EXPT. 1 | | | EXPT. 2 | | | EXPT. 3 | | |
| | −PHA | +PHA | (SI) | −PHA | +PHA | (SI) | −PHA | +PHA | (SI) |
| NIL | 210 | 61,573 | 293 | 344 | 42,927 | 125 | 690 | 73,953 | 107 |
| COMPLEMENT ALONE | 272 | 117,623 | 432 | 606 | 74,319 | 124 | 841 | 116,079 | 138 |
| WM-60 PLUS COMPLEMENT | 221 | 253 | 1 | 225 | 650 | 3 | 107 | 993 | 9 |
| WM-66 PLUS COMPLEMENT | 112 | 190 | 1 | 112 | 319 | 3 | 199 | 228 | 1 |
| WM-66 ALONE | 332 | 84,126 | 253 | 145 | 51,259 | 354 | 416 | 70,313 | 169 |

Footnotes
[a]Peripheral blood mononuclear cells treated with WM-66 or positive MHC Class 1 control (WM-60, then with rabbit serum, or with either WM-66 or serum alone.
[b]Values indicate means of triplicate wells for $1 \times 10^5$ cells incubated in medium alone (−PHA) or in the presence 10 ug/ml PHA (+PHA). SI indicates stimulation index (+PHA)/(−PHA)

The reactivity of WM-63 with haemopoietic and lymphoid cells is outlined in Table 4. WM-63 bound to over 95% of normal peripheral blood mononuclear cells, including virtually all monocytes and T and B-lymphocytes, as well as over 90% of tonsil lymphocytes. A minor proportion of thymic lymphocytes were also reactive with WM-63. Granulocytes, platelets, and erythrocytes were negative. WM-63 also reacted with a minority of bone marrow mononuclear cells. Reactivity with bone narrow granulocyte-macrophage progenitors, however, was more significant, as pretreatment of bone marrow with WM 63 and complement produced a mean 73% reduction in myeloid colony formation (Table 5).

WM-63 was also reactive with a variety of leukaemic cell lines and cases of acute and chronic leukaemia. Cases of B-CLL and T-ALL were most frequently reactive with WM-63, but a significant proportion of cases of acute leukaemia (ALL and AML) were also positive. All non-haemopoietic malignant cell lines tested, however, were negative.

Cytolytic Effect of WM-63 On Lymphocyte Proliferation

WM-63 was capable of lysing virtually all human peripheral blood mononuclear cells, using either rabbit (mean cytotoxicity 99.3% +/−0.2 n=3) or human complement (mean cytotoxicity 96.3% +/−0.5, n=3). When cells were treated with WM-63 and rabbit complement, and subsequently cultured with 10 ug/ml PHA, there was a marked inhibition of lymphocyte proliferative response, indicating that WM-63 was cytotoxic to virtually all mitogen-responsive T lymphocytes (Table 6).

Immunochemical Characterization of the Antigen Recognized By WM-63

Attempts to immunoprecipitate the antigen recognized by WM-63 antibody from 125I-labelled cell surface membrane extracts were unsuccessful.

TABLE 4

REACTIVITY OF WM-63 MAB WITH NORMAL AND LEUKAEMIC HAEMOPOIETIC CELLS

| CELL TYPE | PERCENTAGE POSITIVE[a] |
|---|---|
| (A) NORMAL CELLS | |
| Peripheral blood mononuclears | 97.8 +/− 0.8 (n = 5) |
| T lymphocytes (CD-3+) | 99.4 +/− 0.5 (n = 5) |
| B lymphocytes (CD-20+) | 99.2 +/− 1.0 (n = 5) |
| Monocytes | 98.3 +/− 0.5 (n = 3) |
| Granulocytes | 4.3 +/− 1.5 (n = 6) |
| Platelets | 1 (n = 6) |
| Erythrocytes | 1 (n = 6) |
| Thymocytes | 43.7 +/− 8.0 (n = 3) |
| Tonsil lymphocytes | 90.0 +/− 4.1 (n = 3) |
| Bone marrow mononuclears | 44.0 +/− 3.0 (n = 2) |
| (B) LEUKAEMIC CELLS | |
| AML[c] | 2/6[b] |
| C-ALL | 6/10 |
| T-ALL | 4/5 |
| B-CLL | 6/6 |
| CML | 2/8 |
| Hairy cell leukaemia | 1/1 |
| T-CLL | 1/1 |
| PLL | 1/1 |
| B-lymphoma | 1/1 |
| (C) LEUKAEMIC CELL LINES | |
| MYELOID | 3/4 |
| B-CELL | 3/3 |
| T-CELL | 3/5 |
| PRE-B | 1/3 |
| (D) NON-HAEMOPOIETIC CELL LINES | |
| MELANOMA | 0/1 |
| SQUAMOUS CELL CARCINOMA | 0/2 |
| FALLOPIAN CARCINOMA | 0/1 |
| OVARIAN CARCINOMA | 0/4 |
| CERVICAL CARCINOMA | 0/2 |
| NEUROBLASTOMA | 0/1 |
| MAMARY CARINOMA | 0/1 |

Footnotes
[a]Percentage of cells positive above negative control by indirect immuno-fluorescence, +/− 1 standard deviation.
[b]Number of cases of leukaemia, or number of cell lines, with ≧20% cells positive by indirect immuno-fluorescence, over total number tests.
[c]B-CLL, B form of chronic lymphatic leukaemia; T-CLL, T form of CLL; C-ALL, common or non-T, non-B form of acute lymphoblastic leukaemia; AML, acute myeloid leukaemia; CML, chronic myeloid leukaemia.

TABLE 5

REACTIVITY OF WM-63 WITH NORMAL BONE MARROW MYELOID PROGENITOR CELLS

| TREATMENT OF CELLS | NUMBER OF CFU$_{GM}$ | |
|---|---|---|
| | EXPT. 1 (% inhibition) | EXPT. 2 (% inhibition) |
| IRRELEVANT MAB + C' | 345 (0) | 129 (0) |
| WM-63 Plus complement | 104 (70) | 31 (76) |
| WM-60 Plus complement | 0 (100) | 5 (96) |

TABLE 6

EFFECT OF MONOCLONAL ANTIBODY TREATMENT OF PHA-INDUCED LYMPHOCYTE PROLIFERATION

| CELL[a] TREATMENT | COUNTS PER MINUTE[b] | | | | | | | | |
|---|---|---|---|---|---|---|---|---|---|
| | EXPT. 1 | | | EXPT. 2 | | | EXPT. 3 | | |
| | −PHA | +PHA | (SI) | −PHA | +PHA | (SI) | −PHA | +PHA | (SI) |
| NIL | 5246 | 116,591 | (22) | 3853 | 104,328 | (27) | 584 | 49,750 | (85) |
| COMPLEMENT ALONE | 1642 | 189,189 | (115) | 1484 | 59,556 | (40) | 316 | 120,713 | (206) |
| WM-60 PLUS COMPLEMENT | 214 | 166 | (1) | 584 | 1,769 | (3) | 90 | 225 | (2.5) |
| WM-63 PLUS COMPLEMENT | 167 | 107 | (1) | 106 | 324 | (3) | 120 | 237 | (2) |

Footnotes
[a]Peripheral blood mononuclear cells treated with WM-63 or positive MHC Class 1 control (WM-60, then with rabbit serum, or with either WM-66 or serum alone.
[b]Values indicate means of triplicate wells for 1 × 10$^6$ cells incubated in medium alone (−PHA) or in the presence 10 ug/ml PHA (+PHA). SI indicates stimulation index (+PHA) (−PHA)

by WM-63 antibody from $^{125}$I - labelled cell surface membrane extracts were unsuccessful.

Haemopoietic Tissue Reactivity of WM-63

Frozen sections of normal tissues were evaluated for WM-63 reactivity by immunoperoxidase staining. WM-63 stained macrophages and lymphocytes present in all tissue samples, and labelled the lymphoid areas in spleen, lymph node, tonsil, and thymus. Other tissue elements were not stained, including heart, lung, liver, gut, skin, placenta, breast, brain and salivary gland.

WM-66 reacts with a previously unrecognised human leucocyte differentiation antigen of relative molecular mass of approximately 65 kilodaltons, which is expressed on virtually all matured T and B lymphocytes and monocytes. WM-66 is also strongly cytolytic with either human or rabbit complement, and treatment of peripheral blood lymphocytes with WM-66 and complement effectively abolishes the proliferative response to phytohaemagglutinin. WM-66 reacts with a minority of bone marrow mononuclear leucocytes, and produces some inhibition of granulocyte-macrophage progenitor growth. The distribution of the previously unrecognised 65KD antigen is not completely restricted to haemopoietic and lymphoid cells, as WM-66 also reacted with epithelial cells in sections of bronchus and salivary glands.

A small number of leucocyte antigens of broad non-lineage distribution have been described previously using monoclonal antibodies. Class 1 MHC and leucocyte common antigens (CD-45) are the best characterized of these, and can be distinguished from the 65 kilodalton molecule recognised by WM-66 on a number of criteria. Class 1 MHC molecules are dimers consisting of a heavy chain of relative molecular mass 49 kilodaltons associated with beta-2-microglobulin (12 kilodaltons). On haemopoietic tissues Class I MHC antigens are expressed on platelets, acute leukaemias, and a variety of leukaemic cell lines. Similarly, the molecular weight of CD-45 antigens (relative molecular mass 200 kilodaltons) and expression on cell lines excludes the possibility that WM-66 is reactive with this antigen.

Three other monoclonal antibodies with non-lineage leucocyte reactivity have also been described. PHM-1 reacts with T and B lymphocytes and monocytes/macrophages, but in addition binds to neutrophils and some cell lines. The molecular weight of the antigen binding PHM.1 has been reported as 180/62 kilodaltons.

A 47 kilodalton antigen detected by the Mab HuLy-M3 has also been described. This antibody, however, has weak reactivity with platelets and neutrophils, and with several leukaemic cell lines, properties not shared by WM-66. Finally, the Mab CAMPATH-1 has similarities to WM-66. However, the antigen precipitated by CAMPATH-1 is a variably glycosylated protein of relative molecular mass 23-30 kilodaltons. CAMPATH-1, in addition to reacting with chronic B cell malignancies, also reacts with cases of ALL. It is therefore clear that WM-66 is distinguishable from all of the above non-lineage specific Mabs, and that the 65 kilodalton molecule recognised by WM-66 is a previously unrecognised differentiation antigen.

The human complement-fixing ability of WM-66 is somewhat unusual for a murine Mab. This property has been largely ascribed to rat Mabs, although a few murine Mabs have been reported to fix human complement. Together with the ability of WM-66 to obliterate mitogen-induced lymphocyte proliferation, the human complement-fixing activity of WM-66 suggests potential clinical applications for this reagent in eliminating normal or leukaemic lymphocytes either in vivo or ex-vivo from bone marrow. Although WM-66 does not react with ALL cells, its binding to T lymphocytes and B-CLL cells suggests that it may have a role as an immunosuppressant in vivo, or may be therapeutically useful in B-CLL.

In addition, WM-66 may also be linked to other compounds by heterobifunctional linkages. These compounds include drugs such as Melphalan and Methotrexate; radio isotopes such as Iodine 131 and Yttrium; and toxins such as, ricin and its derivatives and diptheria toxins.

Monoclonal antibody WM-63 has a novel pattern of reactivity with human leucocytes. WM-63 reacts with virtually all normal lymphocytes and monocytes from peripheral blood, but it is unreactive with red blood cells, platelets, granuloctyes, and non-haemopoietic cells from a wide variety of tissued. WM-63 also reacts with a proportion of bone marrow cells, including the majority of granulocyte-macrophage progenitors. In keeping with this pattern of binding to immature leucocytes, WM-63 has extensive reactivity with human acute and chronic leukaemias, lymphoproliferative disorders, and a variety of leukaemic and lymphoblastoid cell lines.

Whilst repeated attempts to immunoprecipitate and characterize the antigen defined by WM-63 have so far been unsuccessful, comparison with other Mabs directed at non-specific leucocyte antigens is therefore based solely on differences in reactivity pattern. However, by these criteria, it is clear that WM-63 reacts with a previously unrecognised leucocyte differentiation antigen.

Class 1 MHC and leucocyte common antigens (CD 45) are clearly distinguishable from the WM-63 reactive antigen on the basis of cell distribution. Class 1 MHC antigens are expressed on platelets as well as a wide variety of non-haemopoietic tissues, whereas WM-63 is clearly unreactive with platelets and with all non-haemopoietic tissues examined. The leucocyte common or T200 antigen detected by CD-45 Mabs is present on granulocytes, which were essentially unreactive with WM-63. Similarly, T200 is expressed on Reh, KM-3 and K-562 cell lines, which are negative with WM-63. CAMPATH 1 is reactive with KM.3 and Reh cell lines, and negative with U937, whilst WM-63 has an opposite pattern of binding with these three cell lines. WM-63 can also be distinguished from PHM.1 and Hu Ly M-3 Mabs by its lack of binding to granulocytes, which are positive with these Mabs. In addition Hu Ly M 3 reacts with KM 3 cells, which are negative with WM-63. This data is summarized in Table 7.

It is clear from this information that WM-63 binds to a previously unrecognised antigen which has a distinctly different cellular distribution from monoclonal antibodies previously described.

A major feature of interest of WM-63 is its high lytic efficiency with either rabbit or human complement. Pretreatment of human peripheral blood lymphocytes with WM-63 and human serum, killed effectively all lymphocytes capable of responding to the mitogen PHA. This property suggests a number of possible roles for WM-63 as a therapeutic agent. The reactivity of WM 63 with all T lymphocytes may make it an effective immunosuppressive when administered in vivo, by virtue of its ability to activate human complement and therefore lyse cells directly.

A further potential application of WM-63 is suggested by its extensive reactivity with leukaemic cells. WM-63 is potentially capable of binding to, lysing, and removing circulating leukaemic cells, and diffusing into bone marrow and other tissues to the same effect. Reactivity with normal myeloid cells may not be a major concern in this instance, as the majority of conventional cytotoxic agents have this effect, but can be administered in carefully controlled dosages to minimize this problem.

TABLE 7

REACTIVITY PATTERNS OF WM-63 AND OTHER MABS WITH NON LINEAGE DISTRIBUTION

| CELL TYPE | WM-63 | MHC CLASS 1 | CD-45 | PHM-1 | HU LY M3 | CAMPATH-1 |
|---|---|---|---|---|---|---|
| Granulocytes | − | + | + | + | + | − |
| Platelets | − | + | − | NT | − | − |
| U 937 | + | + | + | + | + | − |
| KM-3 | − | + | + | NT | + | + |
| K562 | − | + | + | NT | − | − |
| Reh | − | + | + | NT |  | + |

We claim:

1. A mouse monoclonal antibody produced by hybridoma cell line designated F56-2D7 (ECACC 88101104).

2. A hybridoma cell line designated F56-2D7 (ECACC 88101104).

3. A monoclonal antibody produced by a hybridoma cell line designated F56-4D6 (ECACC 88101103).

4. A hybridoma cell line designated F56-4D6 (ECACC 88101103).

* * * * *

UNITED STATES PATENT AND TRADEMARK OFFICE
CERTIFICATE OF CORRECTION

PATENT NO. : 5,158,885

DATED : October 27, 1992

INVENTOR(S) : Kenneth F. Bradstock; Michael K. Atkinson; Anthony J. Henniker

It is certified that error appears in the above-identified patent and that said Letters Patent is hereby corrected as shown below:

Column 1, line 27, change "drammatically" to -- dramatically --.
Column 1, line 40, after "virtually" insert -- all --.

Column 3, line 36, change "F56.4D6" to -- F56-4D6 --.
Column 3, line 45, change "F56.4D6" to -- F56-4D6 --.
Column 3, line 49, change "F56.2D7" to -- F56-2D7 --.
Column 3, line 49, change "F56 4D6" to -- F56-4D6 --.

Column 5, line 8, change "allogeneic" to -- allogenic --.
Column 5, line 16, change "1X10$^6$" to -- 1X10$^5$ --.
Column 5, line 18, after "with" change "an" to -- a --.
Column 5, line 36, change "lystate" to -- lysate --.

Column 6, line 8, change "daiminobenzidine" to -- diaminobenzidine --.
Column 6, line 60, after "(CD-20+" insert a closing parentheses.

Column 8, line 64, change "narrow" to -- marrow --.

Column 9, line 25, change "125I" to -- $^{125}$I --.

Column 10, line 15, change "MAMARY" to -- MAMMARY --.

Column 11, line 32, change "PHM.1" to -- PHM-1 --.

UNITED STATES PATENT AND TRADEMARK OFFICE
CERTIFICATE OF CORRECTION

PATENT NO. : 5,158,885
DATED : October 27, 1992
INVENTOR(S) : Kenneth F. Bradstock; Michael K. Atkinson; Anthony J. Henniker It is certified that error appears in the above-identified patent and that said Letters Patent is hereby corrected as shown below:

```
Column 12, line 6,  change "tissued" to -- tissues --.
Column 12, line 35, change "KM.3" to -- KM-3 --.
Column 12, line 38, change "PHM.1" to -- PHM-1 --.
Column 12, line 40, change "M 3" to -- M-3 --.
Column 12, line 41, change "KM 3" to -- KM-3 --.
Column 12, line 54, change "WM 63" to -- WM-63 --.
```

Signed and Sealed this

Eleventh Day of January, 1994

Attest:

BRUCE LEHMAN

*Attesting Officer*  *Commissioner of Patents and Trademarks*